(12) United States Patent
Stewart et al.

(10) Patent No.: US 6,950,184 B2
(45) Date of Patent: Sep. 27, 2005

(54) WATER QUALITY MONITORING BY RAMAN SPECTRAL ANALYSIS

(75) Inventors: Shona Stewart, Pittsburgh, PA (US);
John S. Maier, Pittsburgh, PA (US);
Patrick J. Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 10/922,006

(22) Filed: Aug. 18, 2004

(65) Prior Publication Data

US 2005/0052645 A1 Mar. 10, 2005

Related U.S. Application Data

(63) Continuation-in-part of application No. 10/823,902, filed on Apr. 14, 2004, which is a continuation of application No. 10/339,807, filed on Jan. 10, 2003, now Pat. No. 6,765,668.
(60) Provisional application No. 60/347,806, filed on Jan. 10, 2002.

(51) Int. Cl.[7] .............................. G01J 3/44; G01N 21/65
(52) U.S. Cl. ...................................................... 356/301
(58) Field of Search ........................................ 356/301

(56) References Cited

PUBLICATIONS

Grow et al, New Biochip Technology for Label–Free Detection of Pathogens and Their Toxins, Journal of Microbiological Methods, vol. 53, Issue 2, May 2003, pp. 221–233.*

* cited by examiner

*Primary Examiner*—F. L. Evans
(74) *Attorney, Agent, or Firm*—Duane Morris, LLP

(57) ABSTRACT

Raman scattering of radiation applied to a water sample is used to assess occurrence of a pathogen in the sample. The method is useful for detecting pathogens that are difficult to detect using other methods, such as protozoa. Examples of organisms that can be detected in water samples using these methods include protozoa of the genus *Cryptosporidium* and the genus *Giardia*. The methods described herein have important applications, such as for detection of *Cryptosporidium* organisms in municipal water systems.

32 Claims, 11 Drawing Sheets

Figure 1:
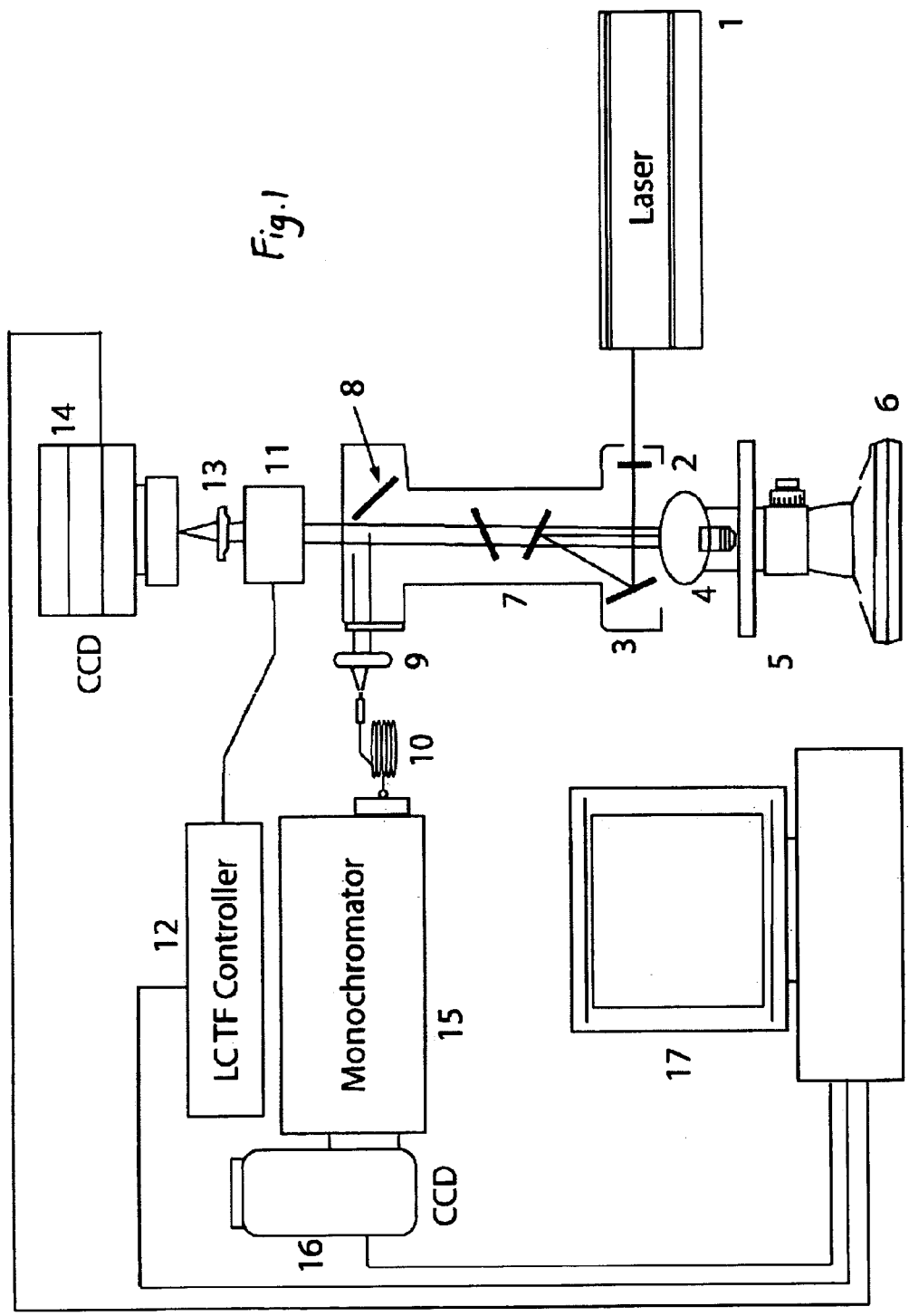
Figure 3A:
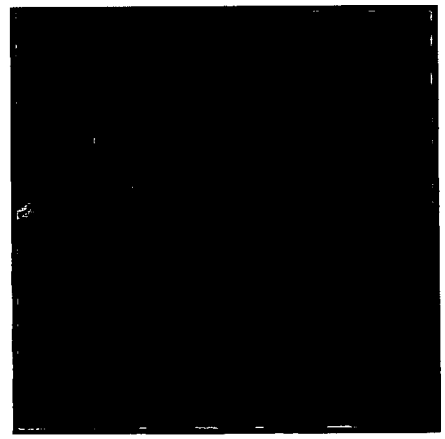
Figure 3B:
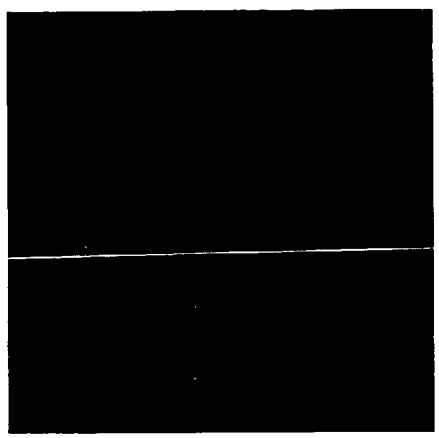
Figure 3C:
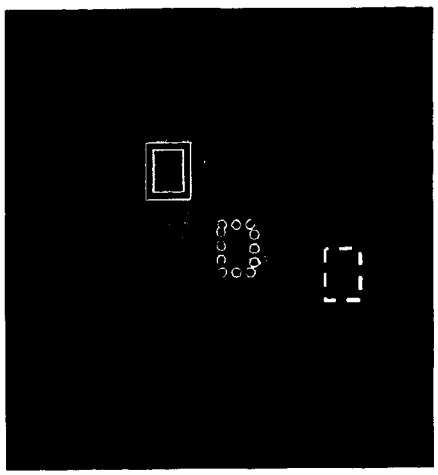
Figure 3D:
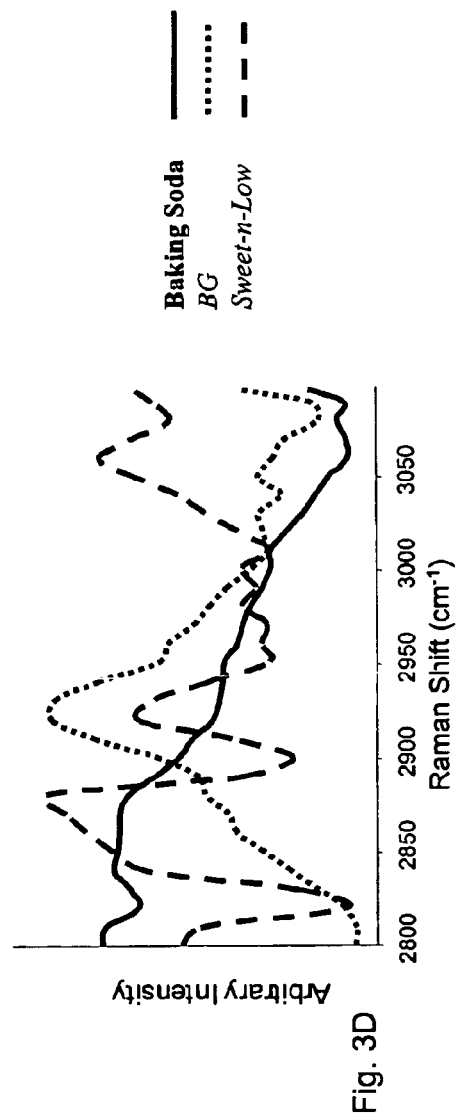

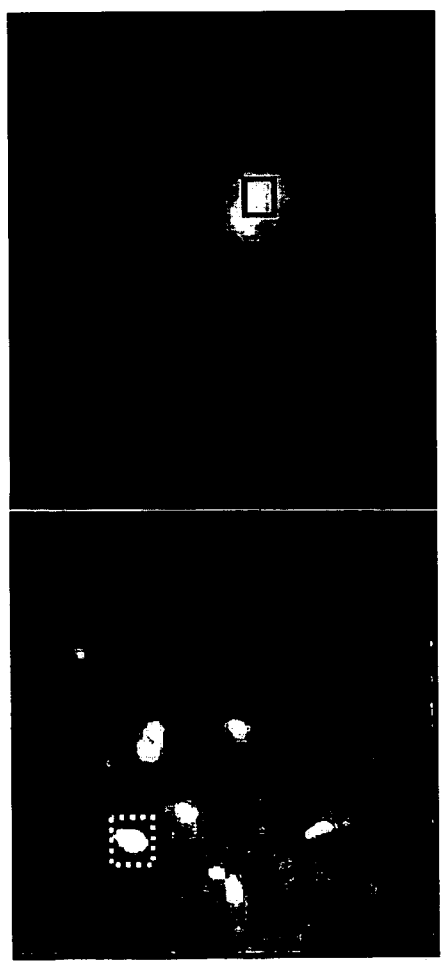
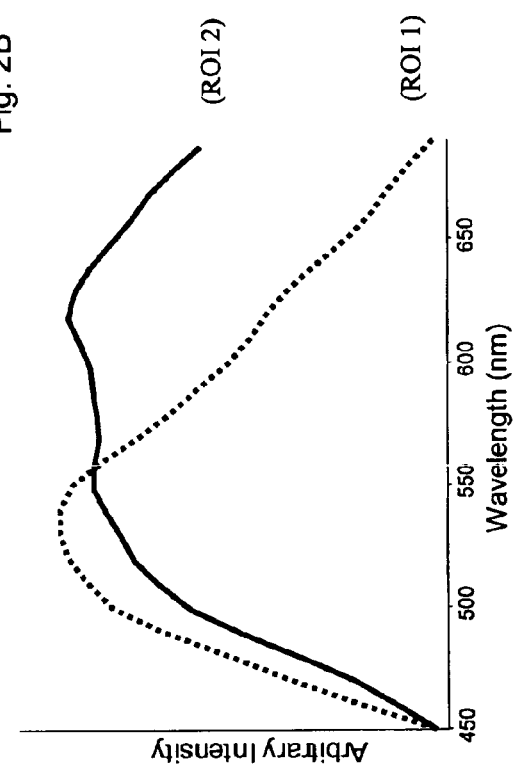
Fig. 2A
Fig. 2B
Fig. 2C

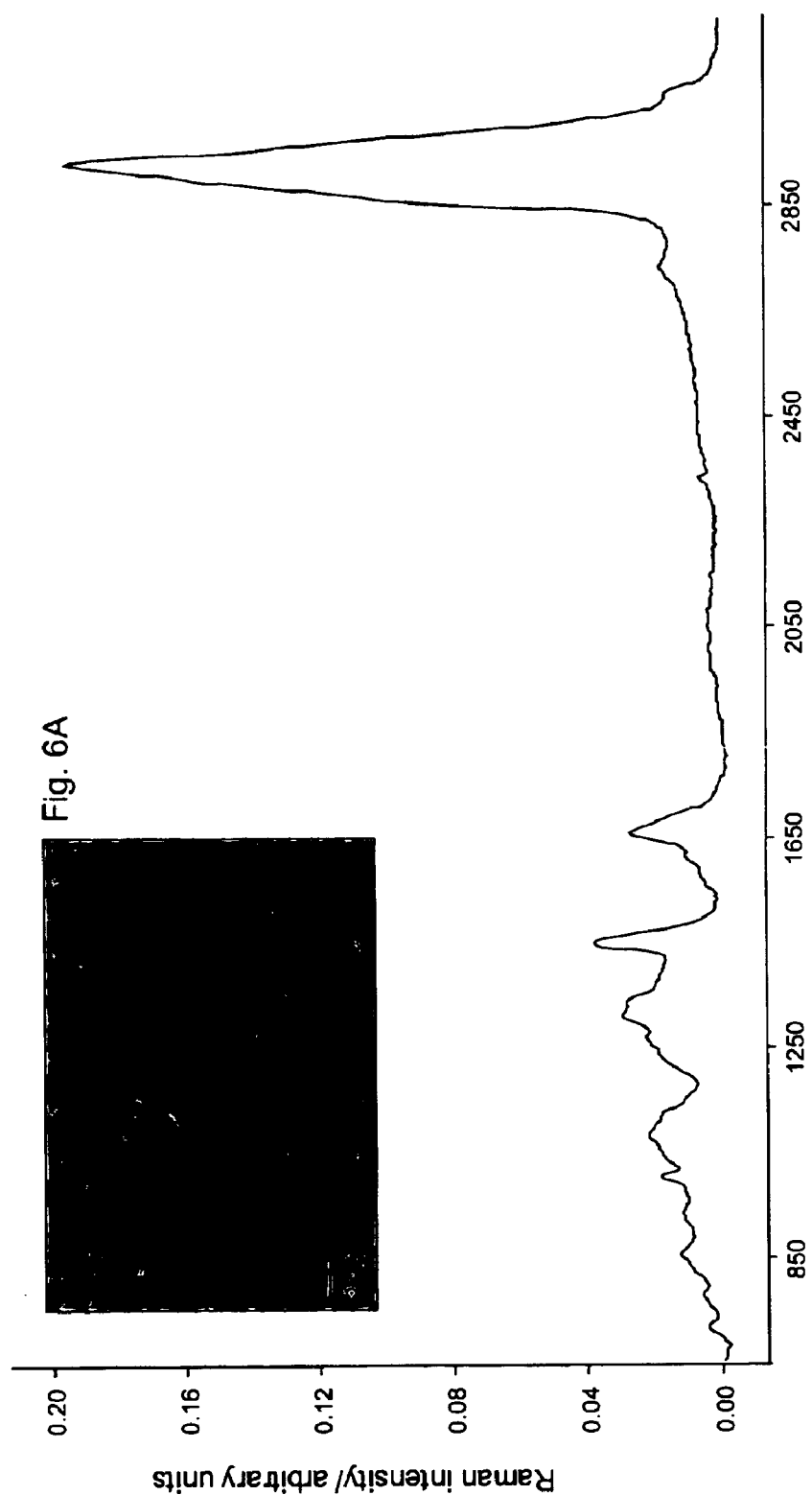

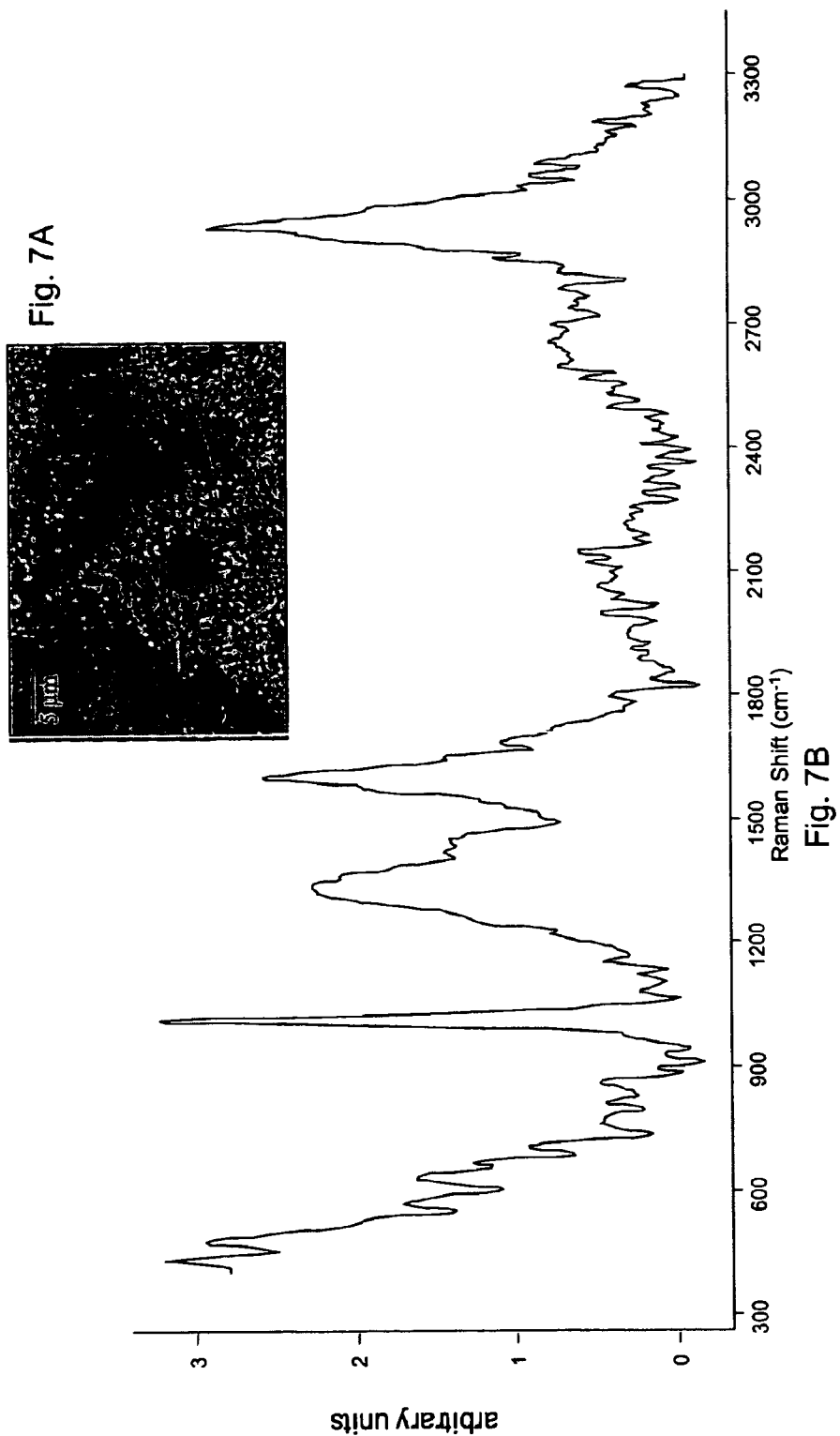

WATER QUALITY MONITORING BY RAMAN SPECTRAL ANALYSIS

CROSS-REFERENCES TO RELATED APPLICATIONS

This application is a continuation-in-part of U.S. application Ser. No. 10/823,902 filed 14 Apr. 2004, which is a continuation of U.S. application Ser. No. 10/339,807, filed 10 Jan. 2003, which is now issued as U.S. Pat. No. 6,765,668, and is entitled to priority pursuant to 35 U.S.C. §119(e) to U.S. provisional patent application No. 60/347,806, which was filed on 10 Jan. 2002. The entirety of each of these applications is incorporated herein by reference.

BACKGROUND OF THE INVENTION

The invention relates generally to the field of assessing occurrence of chemical and biological pathogens in water.

There are two primary sources of drinking water. The first source, ground water, can be extracted either at springs at which it naturally wells up to the surface or from wells sunk into the earth. Surface water is the second source, and is collected from bodies of stationary or moving water on the surface of the earth, such as rivers, lakes, and reservoirs. Ground water ordinarily accumulates by percolating downward from the surface to underground formations, and is naturally filtered such that it rarely contains particulates carried downwards from the surface. On the other hand, particulates which find their way into surface water can remain suspended therein for significant periods of time.

Some particulates, such as bacteria and protozoa, can affect human health. Such particulates are normally removed or neutralized as a part of the water treatment processes applied to water used for municipal or household purposes. Because some particulate pathogens, such as *Cryptosporidium* organisms are resistant to most common chemical water disinfection treatments, it is necessary to rely on filtration to remove enough of the organisms to meet the applicable water quality standards.

Protozoa such as *Cryptosporidium* and *Giardia* organisms can cause serious illness, particularly in individuals having weakened immune systems. In view of the widespread distribution of municipal water sources, it is of critical importance that protozoan contamination of a municipal water supply be quickly detectable, so that appropriate health warnings can be issued prior to infection of significant numbers of individuals.

Current protozoa detection methods rely on concentration of large volumes of water and detection of protozoa in the concentrated sample using immunological methods (e.g., a fluorescently-labeled antibody which binds specifically to a particular protozoan). The results of the immunological testing must be confirmed by microscopic analysis.

There are numerous shortfalls to immunological detection methods. First, the methods are time-consuming, requiring at least hours to perform. The specificity of the method relies entirely on the specificity of the antibody used. If the antibody reacts with numerous targets other than the protozoan of interest, then a large number of false positive results can be obtained—resulting in unnecessary health alerts, excessive analysis of samples, or both. Potentially more seriously, if the antibody reacts with only certain variants of a protozoan, but not with a variant that occurs in the water being sampled, the immunological test can fail to detect the pathogen even when it is present. Furthermore, current immunological tests cannot differentiate between protozoan cysts (or oocysts) that are infective and those that are not, nor between those which are viable and those that are not. Tests to determine whether protozoa will reproduce or infect subjects can also be performed by observing infection and reproduction of the protozoa in mice or other subjects.

Other methods of indicating the presence of protozoan pathogens in water samples are even less specific. For example, measurements of the turbidity of water samples can provide information regarding the overall content of particulates in the water sample, but cannot identify the particulates. Examination of the presence of indicator organisms (e.g., fecal coliform bacteria) can indicate occurrence of generalized contamination of the water sample, but rely on association of protozoan contamination with fecal contamination.

The methods disclosed in this application overcome the shortcomings of prior art methods and enable detection of protozoan and other particulate contaminants in water samples.

*Cryptosporidium*

*Cryptosporidia* are protozoan parasites that can cause severe, acute disease in humans and other animals when the parasites are ingested. Occurrence of the disease requires reproduction of the parasites in the host. In healthy humans, the parasites can cause severe diarrhea, cramping, and discomfort. Although most healthy humans recover readily from *cryptosporidial* infection, immunocompromised individuals (e.g., humans who are ill, taking immunosuppressing drugs, very old, or very young) can be much more severely affected. As demonstrated in known outbreaks, *cryptosporidial* infection can be fatal to immunocompromised patients. There is no specific drug therapy proven to be effective to treat *cryptosporidial* infections. For these reasons, detection of *cryptosporidia* in water supplies is important. It is also important to be able to distinguish viable and non-viable *cryptosporidia* and infectious and non-infectious *cryptosporidia*.

Environmental sources of *cryptosporidia* are not exhaustively understood. However, there is a general understanding that at least most *cryptosporidia* are transmitted by way of fecal contamination, the feces being of either human or animal origin. For this reason, water sources which may at least occasionally be contaminated with treated or untreated sewage or with runoff from agricultural animal farms and ranches are considered to be at significant risk for contamination with *cryptosporidia*.

*Cryptosporidia* may be identified by their reaction with specific antibodies and by their microscopic morphological and staining characteristics. *Cryptosporidia* occur outside the body of an animal primarily in the form of oocysts, which are environmentally stable and resistant particles having a diameter that is typically in the range from about 3–6 micrometers. Each oocyst typically contains four sporozoites, each of which can independently infect a host upon ingestion by the host of the oocyst. Extended exposure to the environment, treatment with certain chemicals, exposure to ultraviolet radiation, and other unknown factors can render sporozoites within an oocyst non-viable (i.e., unable to infect a host upon ingestion of the oocyst).

Microscopic examination of oocysts by a trained expert is a currently known method of differentiating viable and non-viable sporozoites. If an oocyst contains no viable sporozoites, then occurrence of the oocyst in a water supply is not a significant health concern. However, it is difficult to determine by simple microscopic observation whether an oocyst contains any sporozoites, let alone any that are viable. There is currently no practical way of differentiating between oocysts that contain viable sporozoites and those which do not, at least on the scale of municipal water treatment. For this reason, the efficacy of water treatment processes for rendering *cryptosporidia* sporozoites non-viable can not be practically assessed, and chemical or physical treat water supplies to render the sporozoites non-viable cannot be relied upon to produce potable water. A rapid method of differentiating viable and non-viable cryptosporidial sporozoites could render such treatments practical. The present invention overcomes this difficulty.

Raman Spectroscopy

Figure 7C:
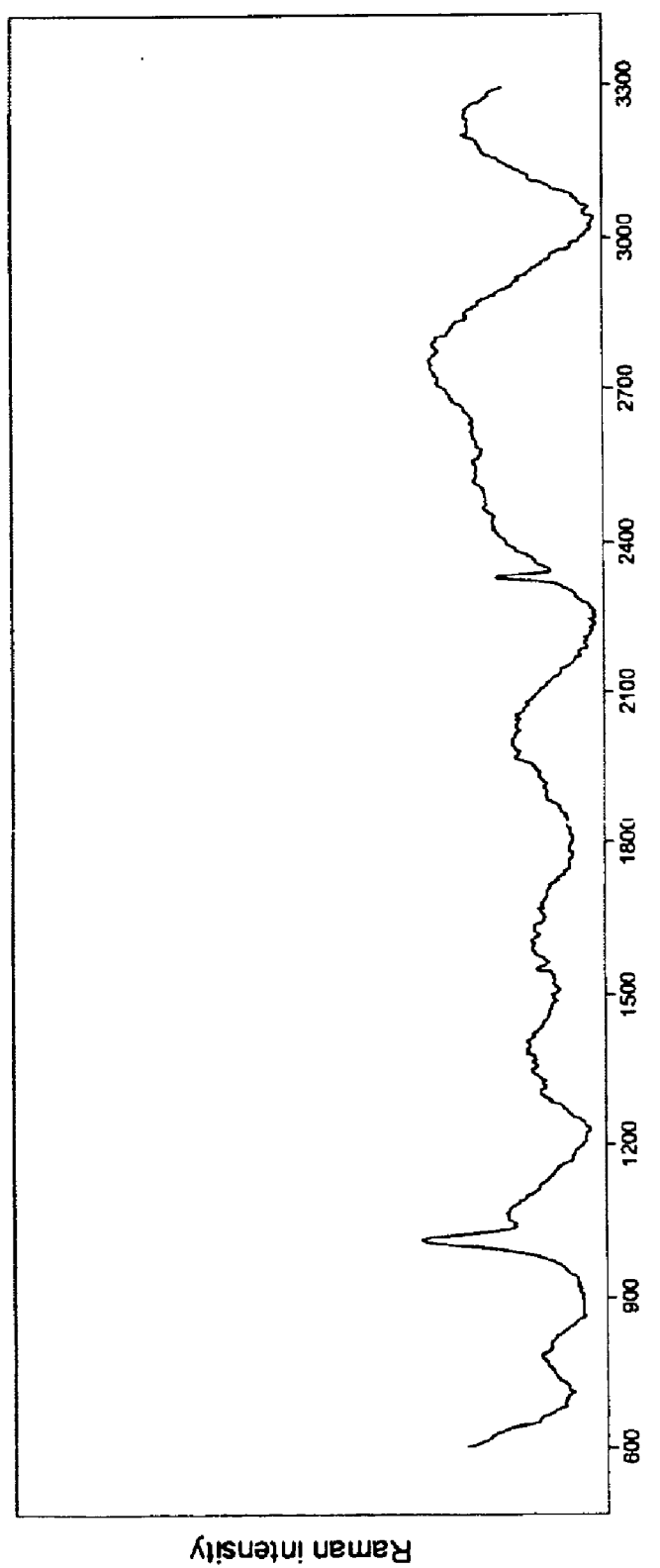

Raman spectroscopy provides information about the vibrational state of molecules. Many molecules have atomic bonds capable of existing in a number of vibrational states. Such molecules are able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in frequency can be more easily distinguished from the Rayleigh scattered light.

Water exhibits very little Raman scattering, and Raman spectroscopy techniques can be readily performed in aqueous environments. Because Raman spectroscopy is based on irradiation of a sample and detection of scattered radiation, it can be used to analyze water samples with little preparation.

An apparatus for Raman Chemical Imaging (RCI) has been described by Treado in U.S. Pat. No. 6,002,476, and in co-pending U.S. patent application Ser. No. 09/619,371, the entirety of each of which is incorporated herein by reference.

BRIEF SUMMARY OF THE INVENTION

The invention relates to method of assessing occurrence of a *Cryptosporidium* oocyst in an aqueous sample. The method comprises irradiating the sample and assessing radiation scattered from the sample for radiation that exhibits a Raman scattering characteristic of *Cryptosporidium* oocysts. Detection of scattered radiation that exhibits a Raman shift characteristic of *Cryptosporidium* oocysts is an indication that a *Cryptosporidium* oocyst occurs in the sample. Scattered light that exhibits a Raman shift (RS) value characteristic of *Cryptosporidium* oocysts can, for example, be light that exhibits an RS value selected from the group consisting of RS values in the range from 500 to 3250 $cm^{-1}$ (e.g., values of about 482, 715, 778, 858, 938, 1000, several peaks, including one strong peak at 1080, forming a broad band between 1012 and 1179, several peaks forming a broad band between 1175 and 1415, including intense peaks at 1270, 1310 and 1330, 1450, 1555, 1575, 1610, several peaks forming a broad band between 1620 and 1783 peaking at 1650, 2620, and several peaks overlapping to form an envelope extending from 2785 to 3180, with the maximum intensity at 2930 $cm^{-1}$ for *C. parvum*). Identifying characteristic Raman scattering can involve assessing multiple RS values or Raman scattered light intensity over a spectrum of RS values (e.g., in one or both of RS value ranges from about 1000 to 1700 $cm^{-1}$ and from 2700 to 3200 $cm^{-1}$), a ratio of intensities at multiple RS values, or some combination of these, for example.

An advantage of the methods described herein is that the methods can distinguish viable pathogens from non-viable ones and infectious pathogens from non-infectious ones. By way of example, it is possible, using the disclosed methods, to distinguish viable *Cryptosporidium* oocysts in a water sample from non-viable oocysts.

Another advantage of the methods described herein is that the sample in which the presence of oocysts is assessed can contain water. Although the sample can be a concentrated or dried water sample, the sample can simply be an untreated water sample taken, for example, from a drinking water source, a municipal water system, or the output of a water treatment facility.

The methods described herein can be performed using Raman spectroscopy equipment described in the art and in the references cited herein. In one embodiment, the sample to be assessed is irradiated with substantially monochromatic visible light. Irradiation with polarized radiation can also be performed.

The methods described herein can be used in combination with methods for ablating *Cryptosporidium* oocysts or rendering them non-viable. Oocysts detected using the methods described herein can be subjected to an agent for ablating them or rendering them non-viable.

BRIEF SUMMARY OF THE SEVERAL VIEWS OF THE DRAWINGS

FIG. 1 is a schematic diagram of an embodiment of the Raman chemical imaging system more fully described in U.S. Pat. No. 6,002,476.

FIGS. 2A and 2B are microscopic fluorescence-spectroscopic images of two different bacterial spore types (*Bacillus pumilis* ROI1 in FIG. 2A; *B. subtilis* ROI2 in FIG. 2B) recorded at different wavelengths, and FIG. 2C is a fluorescent spectrum for the two spore types.

FIG. 3, comprising FIGS. 3A, 3B, 3C, and 3D, shows a Raman chemical image of *Bacillus globigii* spores mixed with baking soda and SWEET-N-LOW (RTM) brand saccharin (FIG. 3C). The three components can readily be discriminated by their Raman spectra (FIG. 3D). Brightfield (FIG. 3A) and polarized light (FIG. 3B) images are shown for reference.

FIG. 4 is a comparison of the Raman spectra of three different strains of *Bacillus anthracis* spores. This figure indicates that Raman spectral analysis can be applied to distinguish between multiple bacterial strains within a single species.

FIG. 5 is a comparison of the Raman spectra of viable, non-viable, and formalin-treated *Bacillus cereus* spores. This figure indicates that Raman spectral analysis can be applied to distinguish between viable and non-viable organisms.

FIG. 6, comprising FIGS. 6A and 6B, are a brightfield image (100× magnification) and a dispersive Raman spectrum, respectively, of substantially pure *Cryptosporidium parvum* oocysts on an aluminum support.

FIG. 7, comprises FIGS. 7A, 7B, and 7C. FIGS. 7A and 7B are a brightfield image (100× magnification), a dispersive Raman spectrum of the entire field shown in the brightfield image, respectively, of a sample containing *Cryptosporidium parvum* oocysts and typical river water interferents on an aluminum support. FIG. 7C is a dispersive Raman spectrum of a comparable field containing only normal interferents obtained from the same river.

Figure 8A:
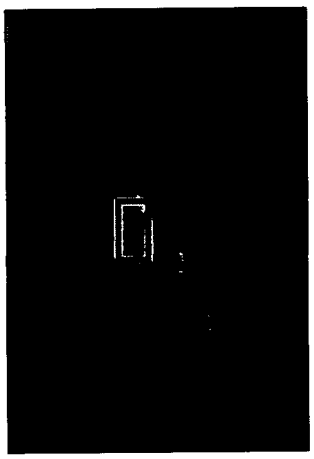
Figure 8B:
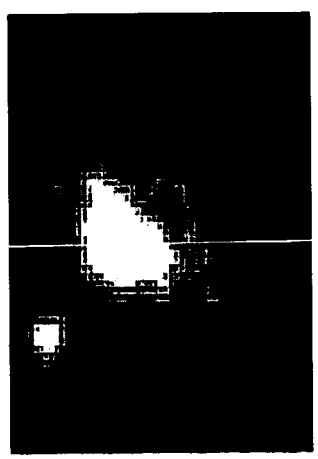
Figure 8C:
Figure 8D:
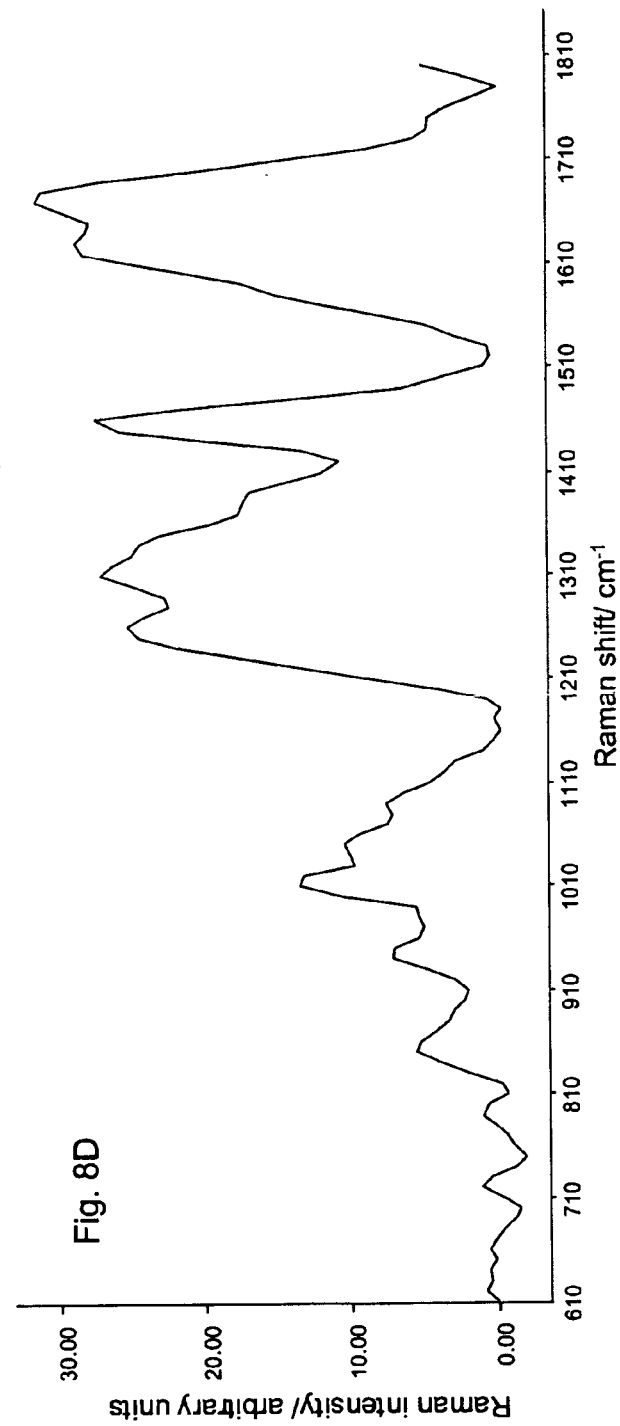

FIG. 8 comprises FIGS. 8A, 8B, 8C, and 8D. FIG. 8A is a brightfield image (100× magnification) of substantially pure *Cryptosporidium parvum* oocysts on an aluminum support. FIG. 8B is a Raman chemical image (assessed at a Raman shift value of 1450 centimeters$^{-1}$ of the microscopic field shown in FIG. 8A. FIG. 8C is an overlay of the images shown in FIGS. 8A and 8B. FIG. 8D is a Raman spectrum obtained from the boxed area of the image shown in FIG. 8B.

Figure 9A:
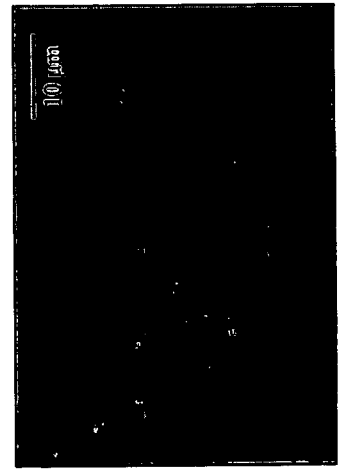
Figure 9B:
Figure 9C:
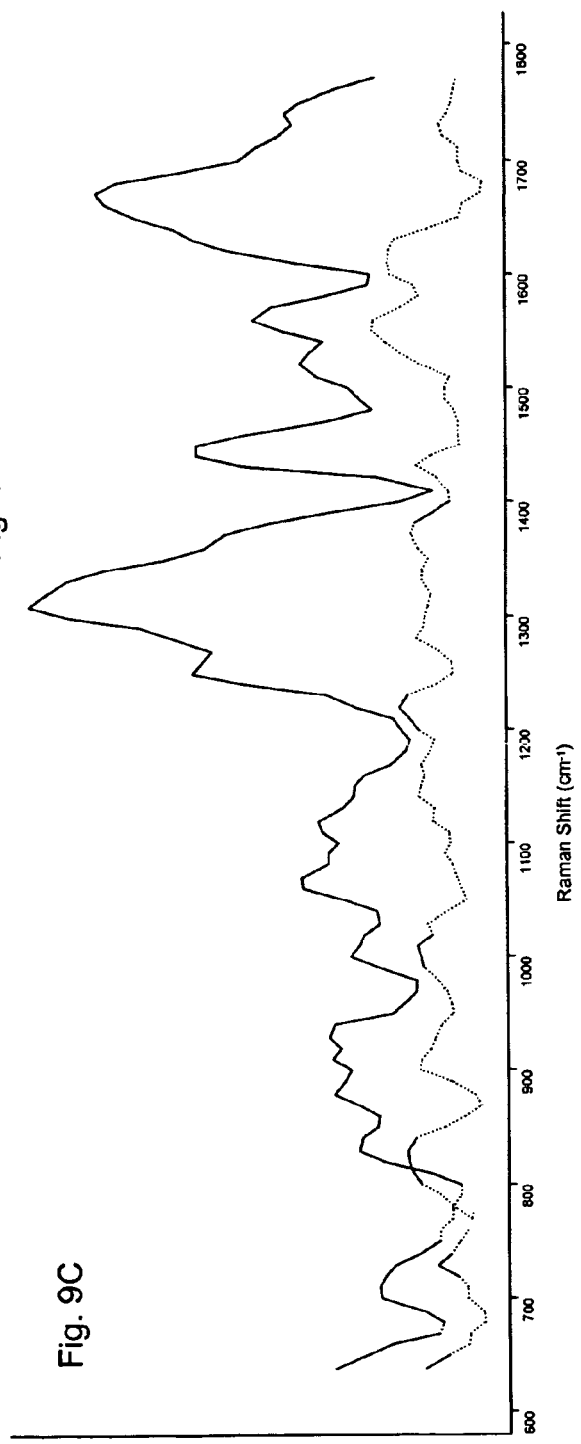

FIG. 9 comprises FIGS. 9A, 9B, and 9C. FIG. 9A is a brightfield image (100× magnification) of substantially pure *Cryptosporidium parvum* oocysts on an aluminum support. FIG. 9B is a Raman chemical image (assessed at a Raman shift value of 1310 centimeters$^{-1}$ of the microscopic field shown in FIG. 9A. FIG. 9C is a pair of Raman spectra obtained from the boxed areas of the image shown in FIG. 9B—one corresponding to an area including an apparent *C. parvum* oocyst, the other corresponding to an area apparently lacking any *C. parvum* oocyst.

Figure 10:
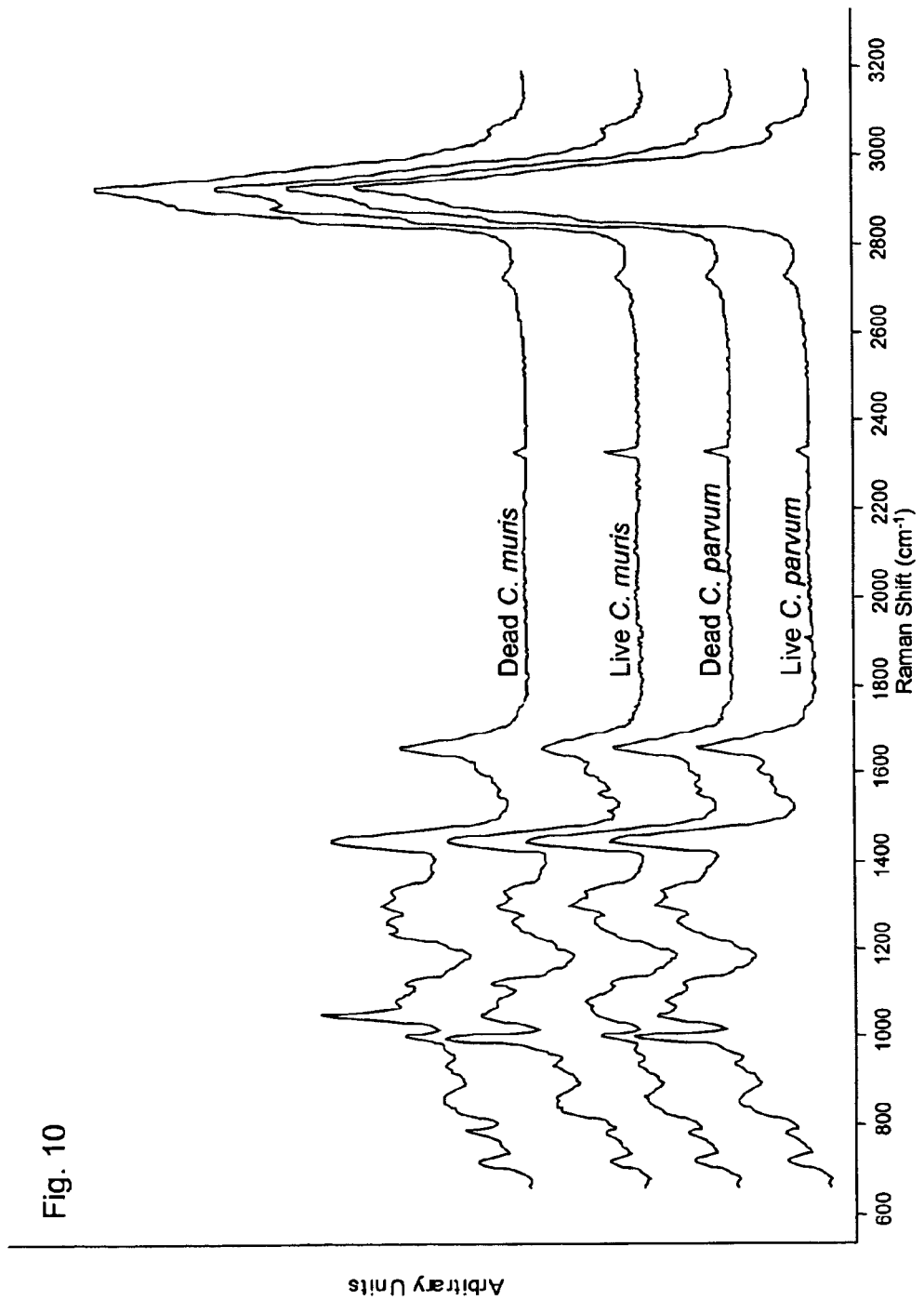

FIG. 10 is a set of four vertically offset dispersive Raman spectra obtained separately from oocysts of *Cryptosporidium muris* and *C. parvum*. Oocysts indicated as "dead" were treated with formalin. Oocysts indicated as "live" were not so treated.

DETAILED DESCRIPTION OF THE INVENTION

The invention is based, in part, on the discovery that irradiation of a water sample containing a pathogen induces Raman scattering of the applied radiation by the pathogen. Raman scattered radiation characteristic of the pathogen can be detected at very low pathogen loads, and the scattered radiation is not significantly inhibited by the water or normal constituents of surface water sources.

The methods described herein involve irradiating a water sample, such as water obtained from a surface water source and concentrated using a 1 micron (micrometer) filter, with substantially monochromatic light and assessing Raman light scattering from the sample. The intensity of Raman light scattering at one or more Raman shift values can be assessed by itself. However, a more information-rich image can be made by combining the Raman scattering data with visual microscopy data to make a hybrid image. In such an image, Raman scattering information can be combined with information derived from the visual microscopic image data, and the superimposed and/or integrated data sets can be assessed together.

The methods described herein allow quantitative evaluation of pathogen loads in a water sample with relatively little and uncomplicated sample preparation, or even without sample preparation. The methods are also capable of distinguishing viable pathogen cells and particles from non-viable cells and particles and infectious pathogen cells and particles from non-infectious cells and particles. The methods described herein have important applications, such as for detection of *Cryptosporidium* organisms in municipal water systems.

Definitions

As used herein, each of the following terms has the meaning associated with it in this section.

"Bandwidth" means the range of wavelengths in a beam of radiation, as assessed using the full width at half maximum method.

"Bandpass" of a detector or other system means the range of wavelengths that the detector or system can distinguish, as assessed using the full width at half maximum intensity method.

The "full width at half maximum" ("FWHM") method is a way of characterizing radiation including a range of wavelengths by identifying the range of contiguous wavelengths that over which the magnitude of a property (e.g., intensity or detection capacity) is equal to at least half the maximum magnitude of that property in the radiation at a single wavelength.

"Spectral resolution" means the ability of a radiation detection system to resolve two spectral peaks.

A protozoan sporozoite, cyst, or oocyst is "viable" if the sporozoite (or a sporozoite contained within the cyst or oocyst) is able to infect a normal host of the protozoan upon ingestion by the host of the cyst or oocyst and continue the life cycle of the protozoan, including production of a cyst or oocyst from the sporozoite in the host.

A protozoan sporozoite, trophozoite, cyst, or oocyst is "infectious" if the sporozoite or trophozoite (or a sporozoite or trophozoite contained within the oocyst or cyst) is able to infect a normal host of the protozoan upon ingestion by the host of the cyst or oocyst and cause a clinical symptom of infection by the protozoan.

DETAILED DESCRIPTION

Raman Spectroscopic Analysis for Detection of Pathogens in Water

The invention is based, in part, on the discovery that irradiation of a water sample containing a pathogen induces Raman scattering of the applied radiation by the pathogen. Raman scattered radiation characteristic of the pathogen can be detected at very low pathogen loads, and the scattered radiation is not significantly inhibited by the water or normal constituents of surface water sources.

The method can be exemplified using *Cryptosporidium* oocysts as an example of the pathogen to be detected. In order to assess occurrence of a *Cryptosporidium* oocyst in a water sample (or in any other aqueous sample), the sample is irradiated and radiation scattered from the sample is assessed for radiation that exhibits a Raman scattering characteristic of *Cryptosporidium* oocysts. Detection of scattered radiation that exhibits a Raman shift characteristic of *Cryptosporidium* oocysts is an indication that a *Cryptosporidium* oocyst occurs in the sample. A Raman spectrum of *Cryptosporidium parvum* oocysts is shown in FIG. 6. Similar spectra can be obtained for any water-borne pathogen using the methods disclosed herein and/or known in the art.

In order to assess whether an entity in a water sample is a pathogen, any of a variety of Raman scattering characteristics of the pathogen can be used. Such characteristics can be identified by assessing the Raman scattering behavior of a pure culture of the pathogen if they are not previously known. Because Raman scattering characteristics of pathogens are substantially invariant from sample to sample, the characteristics of a pathogen of interest can be stored (e.g., by recording characteristic Raman shift (RS) values in a computer memory device). If a source of the pathogen of interest is known (e.g., runoff from a particular farm or wastewater treatment facility), then a sample obtained directly from that source can be assayed as a control to account for any minor variations that might be attributable to local conditions.

An example of a suitable Raman spectral characteristic that can be used to identify a pathogen in a water sample is a Raman shift (RS) value characteristic of the pathogen. Such RS values can be detected in any suitable range, based on the detection equipment used. For example, the equipment described herein and in the patent documents incorporated herein by reverence can be used to detect RS values in the range from near zero to 3500 cm$^{-1}$ (or 500 to 3250 cm$^{-1}$). In order to avoid Raman spectral characteristics of interferents, for example, a plurality of discontinuous Raman spectra may be obtained, such as spectra from 250 to 1800 cm$^{-1}$ (or 1000 to 1700 cm$^{-1}$) and from 2700 to 3500 cm$^{-1}$ (or 2700 to 3200 cm$^{-1}$).

Confidence in the identification of a particle in a water sample as a pathogen of interest can be increased by assessing Raman spectral data at more than one RS value, such as by assessing scattering at two RS values or over a spectrum of RS values. Other informative measures include comparing ratios of Raman scattering intensity at two RS values or at multiple pairs of RS values, such values being comparable with known values or values obtained from a reference sample. Further information can be derived by comparing the shapes of one or more Raman scattering intensity peaks with peaks in known reference spectra or spectra obtained from one or more reference samples. By way of specific example, *Cryptosporidium parvum* oocysts can be detected by assessing the sample at one or more Raman shift values at which peaks are seen in FIG. 6, such as one or more RS values of about 1000, 1080, 1310, 1330, 1450, 1660, 2720, and 2930 cm$^{-1}$. Other RS values which can be assessed to aid identification include values of about 482, 715, 778, 858, 938, several peaks forming a broad band between 1012 and 1179, several peaks forming a broad band between 1175 and 1415, 1270, 1555, 1575, 1610, several peaks forming a broad band between 1620 and 1783,1650, 2620, and a broad band between 2785 and 3180 cm$^{-1}$.

Where interferents of known or predictable composition are present in the water sample, it can be advantageous to avoid assessing Raman spectral information at RS values characteristic of the interferents. For example, FIG. 7A shows a microscopic image of a single *C. parvum* oocyst in a sample containing river water interferents. A dispersive Raman spectrum of the entire field of view of FIG. 7A is shown in FIG. 7B. The presence of interferents can be seen by comparing the Raman spectra of FIGS. 7B and 6B.

There are multiple ways of obtaining useful information regarding occurrence of a pathogen in a sample containing interferents, such as the sample used to generate the information shown in FIG. 7. For example, an RS value at which the pathogen exhibits a greater intensity of Raman scattering than the interferent (e.g., RS=ca. 2930 centimeters$^{-1}$ in FIG. 7B) can be used to assess occurrence of the pathogen.

Alternatively, Raman spectral analysis can be performed on a narrower field in order to obtain a more detailed image of the composition of the components in the field. By way of example, the brightfield image in FIG. 7A shows an area measuring approximately 20×30 micrometers (i.e., ca. 600 square micrometers). If 600 square-micrometer sections of a water sample were assayed for significant Raman scattering, then sections (e.g., that shown in FIG. 7A) that exhibit significant Raman scattering intensity at an RS value characteristic of *C. parvum* can be selected for finer-scale Raman analysis. For example, the spatial resolution of the Raman chemical imaging system disclosed in U.S. Pat. No. 6,002, 476 is on the order of 250 nanometers. Thus, sub-portions of an area such as that shown in FIG. 7A can be assessed at a resolution approaching ⅛ of a square micrometer. An iterative assessment scheme can be used, wherein Raman scattering analyses are made for portions and sub-portions of decreasing size, the assessments being made only for portions and sub-portions which exhibited a pathogen-consistent Raman scattering property in the previous iteration.

As yet another alternative, subtractive Raman spectroscopy can be performed, wherein Raman scattering can be assessed for a control sample known (e.g., by intensive microscopic analysis and/or immunological testing) to be devoid of the pathogen. The Raman scattering data obtained from that control sample (or from an averaged plurality of such control samples, for example) can be subtracted from samples obtained from similar sources (i.e., sources in which the same interferents would be expected, such as the same reservoir) in order to assess occurrence of the pathogen in those samples. In a variant of this method, separate Raman spectral data sets can be gathered from a portion of a microscopic image that is consistent with the presence of a pathogen (e.g., occurrence of 2–6 micrometer diameter spheres if assessing occurrence of *C. parvum*) and from one or more portions of the same image that are not consistent with the presence of the pathogen (e.g., absence of *C. parvum*-like spheres).

Figure 5:
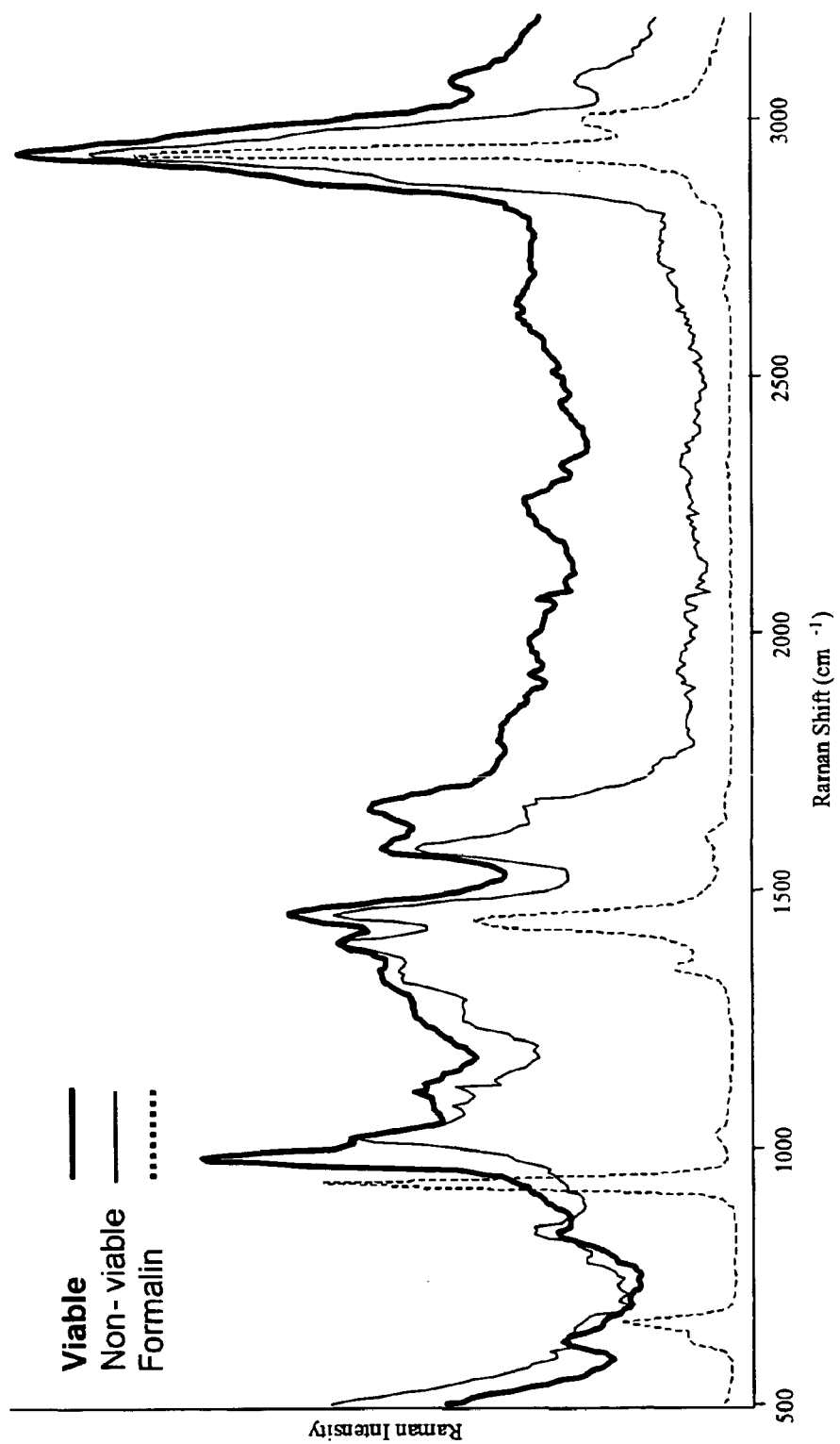

As shown in FIGS. 5 and 10, viable and non-viable forms of a pathogen can be differentiated by their Raman spectra. This characteristic enables discrimination between viable and non-viable pathogen cells or particles in a water sample. For example, the methods can be used to assess a Raman scattering characteristic that is exhibited by viable *Cryptosporidium* oocysts, but not (or to a lesser degree) by non-viable oocysts, or vice versa. Similarly, Raman spectral differences between infectious and non-infectious oocysts can be exploited to differentiate between those forms. By way of example, differences in Raman spectral intensities at RS values of about 970, 1000, 1050, and 1610 centimeters$^{-1}$ can be used to distinguish viable from non-viable oocysts.

Sample Preparation

The methods described herein involve assessing light scattered by a sample. For that reason, the methods can be performed on wide variety of samples. No formal sample preparation is necessary The methods can be performed using a water sample drawn directly from a source. Alternatively (and preferably in situations in which any pathogen is expected to be present in minute quantities, if present at all), a water sample taken from a source can be concentrated prior to Raman spectral analysis of the concentrated sample. Alternatively, particles in a water sample can be collected on a surface, such as by filtering the sample through the surface (e.g., using a 1-micron pore size filter medium), drying the sample against the surface, centrifuging the sample to deposit particles contained therein on the surface, precipitating particles in the sample onto the surface, or some combination of these. Such surfaces can be subjected to Raman spectral analysis in a wet, dehumidified, or dried state.

Raman scattering by articles on or above a surface can be assessed through three dimensions. The instruments described herein and in U.S. Pat. No. 6,002,476 gather Raman scattered light from a single plane that is arranged in focus with a scattered light detector. By varying the focal plane, Raman scattering from particles in different planes can be assessed. When the focal planes that are scattered are nearer to one another than the size of a particle (e.g., a *C. parvum* oocyst has a typical diameter of about 5 micrometers), then Raman spectral information about the interior of the particle can be obtained. By way of example, if Raman spectral data are obtained at multiple parallel focal planes that intersect a *C. parvum* oocyst, then the Raman characteristics (including viability-correlated Raman characteristics) of the sporozoites can be distinguished from one another. In this way, a more accurate assessment of the total number of viable sporozoites in a population of oocysts can be obtained. This information can be used to assess the efficacy of viability-inhibiting agents on *C. parvum* sporozoites. In view of the fact that even a single viable sporozoite contained within a cryptosporidial oocyst can infect a subject, this level of detail is not required. In many instances, it is sufficient to assess whether *cryptosporidial* oocysts contain any viable sporozoites at all.

When particles in a water sample are assessed on a surface, the surface can be substantially any material that does not significantly interfere with Raman spectral analysis. Examples of suitable surfaces are filtration media, ultrafiltration membranes, aluminum-coated glass slides of the type commonly used for Raman spectral analysis, and media (e.g. surfaces coated with colloidal metal particles, such as colloidal gold or silver particles) designed to enhance Raman spectral signals. All of these surfaces are known in the art.

Water-borne Pathogens

The methods described herein can be used to assess occurrence in a water sample of substantially any pathogen that exhibits an identifiable Raman spectral characteristic. Examples of pathogens that can be detected in water samples using the methods described herein include protozoa such as those of the genus *Cryptosporidium* and the genus *Giardia*; bacteria such as *Escherichia coli, Yersinia pestis, Francisella tularensis, Brucella* species, *Clostridium perfringens, Burkholderia mallei, Burkholderia pseudomallei, Chlamydia psittaci, Coxiella burnetii, Rickettsia prowazekii, Vibrio* species; *Enterococcus faecalis; Staphylococcus epidermidis; Staphylococcus aureus; Enterobacter aerogenes; Corynebacterium diphtheriae; Pseudomonas aeruginosa; Acinetobacter calcoaceticus; Klebsiella pneumoniae; Serratia marcescens*; yeasts such as *Candida albicans*; and viruses, including filoviruses such as Ebola and Marburg viruses, naviruses such as Lassa fever and Machupo viruses, alphaviruses such as Venezuelan equine encephalitis, eastern equine encephalitis, and western equine encephalitis, rotoviruses, calciviruses such as Norwalk virus, and hepatitis (A, B, and C) viruses, and biological warfare agents such as smallpox (i.e., *variola major* virus). The methods described herein can be used to distinguish between viable and non-viable forms of these organisms and between infectious and non-infectious forms.

An important group of organisms which the methods described herein are useful for detecting are protozoa of the genus *Cryptosporidium*. At least several species of cryptosporidia are potentially pathogenic in humans, including *Cryptosporidium parvum* (common host: humans), *Cryptosporidium muris* (common host: mice), *Cryptosporidium meleagridis* (common host: turkeys), *Cryptosporidium wrairi* (common host: guinea pigs), *Cryptosporidium felis* (common host: cats), *Cryptosporidium serpentis* (common host: snakes), *Cryptosporidium nasorum* (common host: fish), *Cryptosporidium baileyi* (common host: chickens), *Cryptosporidium sarophilum* (common host: lizards), *Cryptosporidium canis* (common host: dogs), and *Cryptosporidium andersoni* (common host: cattle). The methods described herein are useful for detecting each of these species of *Cryptosporidium*. Using pure cultures as standards, for example, many, if not all, of these species can be differentiated from one another using the methods described herein.

The methods described herein can be used to distinguish different species of cryptosporidia. Many species of cryptosporidia and other pathogens are normally harbored by host animals of a certain genus or even species. By detecting the particular species of a pathogen such as a *Cryptosporidium* in a water source, it is possible to obtain information regarding a likely source or likely sources of the pathogens in the water. By way of example, detection of *C. andersoni* oocysts in a lake suggests that runoff from an agricultural ranch in the lake's watershed may be a source of the oocysts. Any intraspecies differences that can be detected using the methods described herein can furthermore be used to localize a pathogen to a particular source or environment if those differences can be correlated with the source or environment.

Pathogen Ablation and Manipulation

In addition to identifying pathogens at one or more particular locations in a sample, the methods described herein can be used to manipulate the portion of the sample containing the identified pathogen. Pathogens identified using these methods can be ablated or manipulated by directing appropriate ablation or manipulation modalities to the portion of the sample containing the pathogen. By way of example, laser light of sufficient intensity to ablate (i.e., lyse or render non-infectious or non-viable) a *Cryptosporidium* oocyst can be directed to a portion of a sample at which such an oocyst was detected. The same effect can be achieved by activating a heating element which underlies the portion of the sample in which the pathogen was detected. Similarly, a fluid- or particle-collecting device can be directed to the pathogen-containing portion of the sample for the purpose of collecting the pathogen. Alternatively, a radiation source can be activated to melt, or chemically activate, a portion of the substrate adjacent a detected pathogen in order to fix the pathogen to the substrate.

In another embodiment, Raman spectral analysis can be performed on a fluid medium contained on or in a microfluidic circuit, such as one of those described in the co-pending patent application filed 18 Aug. 2004 by Tuschel et al. and entitled "Method and Apparatus of Chemical Imaging in a Microfluidic Circuit." The results of such analysis can be sent to a controller which can control the disposition of fluid in the circuit based on such results, for example.

Raman Spectral Analysis

In order to detect Raman scattered light and to accurately determine the Raman shift of that light, the water sample should be irradiated with substantially monochromatic light, such as light having a bandwidth not greater than about 1.3 nanometers, and preferably not greater than 1.0, 0.50, or 0.25 nanometer. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light) can limit the ability to resolve, detect, or distinguish spectral features. The skilled artisan understands that and how the separation and shape of Raman scattering signals can determine the acceptable limits of spectral resolution for the system for any of the Raman spectral features described herein.

In general, the wavelength and bandwidth of light used to illuminate the sample is not critical, so long as the other optical elements of the system operate in the same spectral range as the light source. For a diffraction grating, the spectral resolution is defined as the ratio between the wavelength of interest and the separation, in the same units as the wavelength, required to distinguish a second wavelength. With a broader source (or a source filter enabling passage of light exhibiting an intensity profile characterized by a greater full width half maximum), greater peak separation is required, because the Raman peaks are more blurred on account of the greater variety of irradiating wavelengths that are shifted. Such a system would have a lower Raman peak resolving power. An ordinarily skilled artisan can calculate the minimum resolving power required for distinguishing two Raman peaks.

The source of substantially monochromatic light is preferably a laser source, such as a diode pumped solid state laser (e.g., a Nd:YAG or Nd:YVO$_4$ laser) capable of delivering monochromatic light at a wavelength of 532 nanometers. Other lasers useful for providing substantially monochromatic light having a wavelength in the range from about 220 to 1100 nanometers (or in a narrower range, such as 280 to 695 nanometers) include HeNe (630 nanometers), argon ion (532 nanometers), argon gas (360 nanometers), HeCd (442 nanometers), krypton (417 nanometers), and GaN (408 nanometers, although doped GaN lasers can provide 350 nanometers). Other lasers can be used as well, such as red diode lasers (700–785 nanometers) and eximer lasers (200–300 nanometers). Known frequency-doubling or -tripling methods can be used in conjunction with lasers (e.g., argon or YAG lasers) to produce shorter wavelengths and optically coherent light. Use of ultraviolet irradiation can permit use of resonance Raman techniques, which can yield more intense signals and simplified spectral peaks. However, lasers capable of ultraviolet irradiation tend to be very costly and complex to use, limiting their desirability. Such lasers also tend to photodegrade biomaterials, rendering them unsuitable for some applications.

Because Raman scattering peaks are substantially independent of the wavelength of the illumination source, the wavelength of light used to irradiate the cells is not critical. However, the illumination wavelength influences the intensity of the Raman peaks, the fluorescent background signals detected, and the susceptibility to laser-induced photodegradation.

Wavelengths at least as low as about 500 nanometers (e.g., from 350 to 695 nanometers), and likely as low as 220 or 280 nanometers, can be used. Because the intensity of scattered light is known to be dependent on the fourth power of the frequency (i.e., inverse wavelength) of the irradiating light, and only proportional to the intensity of the irradiating light, lowering the wavelength of the irradiating light can have the effect of increasing scattering signal output even if the intensity of the irradiating light is decreased. Thus, even under constant illumination, cells can survive irradiation if the intensity of the irradiating light is carefully controlled. Irradiation using even shorter wavelengths can be performed without harming the illuminated cells if intermittent or very short duration irradiation methods are employed. If survival of pathogen cells or oocysts beyond the time of detection is not critical, then the effect of irradiating light on the pathogen need not be considered, at least so long as the Raman spectral features are not significantly affected.

An appropriate irradiation wavelength can be selected based on the detection capabilities of the detector used for assessing scattered radiation. Most detectors are capable of sensing radiation only in a certain range of frequencies, and some detectors detect frequencies in certain ranges less well than they do frequencies outside those ranges. In view of the Raman shift values that can be expected from pathogens in water samples, as disclosed herein, many combinations of light sources and detectors will be appropriate for use in the systems and methods described herein. By way of example, front- and back-illuminated silicon charge coupled device (CCD) detectors are useful for detecting Raman scattered light in combination with irradiation wavelengths described herein.

Assessment of Raman scattered light can be measured using any known detector appropriate for sensing radiation of the expected wavelength (i.e., about 5 to 200 nanometers greater than the wavelength of the irradiating radiation, or near zero to 500 nanometers for other detectors). In view of the relatively low intensities of many Raman scattered light signals, a highly sensitive detector, such as one or more cooled charge-coupled device (CCD) detectors. For parallel operation, CCD detectors having multiple pixels corresponding to discrete locations in the field of illumination can be used to enable simultaneous capture of spectroscopic data at all pixel locations in the CCD detector.

A water sample can be irradiated by the light source in a diffuse or focused way, using ordinary optics. In one embodiment, light from the source is focused on a narrow portion of the sample and Raman scattering from that portion is assessed. In another embodiment, the light used to irradiate the sample is focused on a larger portion of the sample (e.g., a portion large enough to include multiple pathogen particles) or the entire sample. Wide-field illumination allows the acquisition of data and assessment of Raman scattering across the illuminated field or, if coupled with wide-field, massively parallel detectors, can permit rapid Raman scattering analysis across all or part of the illuminated field. In contrast, scanning spot methods to detect Raman scattering require high laser power densities focused into a small region.

The maximum useful power density of irradiation depends on the need for post-Raman scattering use of any pathogen particles that may be detected and the anticipated duration of irradiation. The duration and power density of irradiation must not combine to render the irradiated pathogen particles unsuitable for any desired post-assessment use. The skilled artisan is able to selected irradiation criteria sufficient to avoid these effects.

Spectral image analysis of Raman scattering on the scale of individual pathogen cells, oocysts, or viruses can be performed using known microscopic imaging components. High magnification lenses are preferred, owing to their higher light collection relative to low magnification lenses. The numerical aperture of the lens determines the acceptance angle of light into the lens, so the amount of light collected by the lens varies with the square of the numerical aperture for a fixed magnification. The magnification also determines how much of the laser illuminated area can be observed in the lens. In view of the fact that Raman scattered light can have a relatively low magnitude, selection of an appropriate lens can improve low level signal detection.

Pathogen particles can include many chemical species, and irradiation of such particles can result in Raman scattering at a variety of wavelengths. In order to determine the intensity of Raman scattered light at various RS values, scattered light corresponding to other RS values must be filtered or directed away from the detector. A filter, filter combination, or filter mechanism interposed between the irradiated sample and the detector. The system (i.e., taking into account the bandwidth of the irradiating radiation and the bandpass of any filter or detector) should exhibit relatively narrow spectral resolution (preferably not greater than about 1.3 nanometers, and more preferably not greater than about 1.0, 0.5, or 0.25 nanometers) in order to allow accurate definition and calculation of RS values for closely spaced Raman peaks. If selectable or tunable filters are employed, then they preferably provide high out-of-RS band rejection, broad free spectral range, high peak transmittance, and highly reproducible filter characteristics. A tunable filter should exhibit a spectral resolving power sufficient for Raman spectrum generation (e.g., a spectral resolving power preferably not less than about 12–24 $cm^{-1}$; higher and lower values can be suitable, depending on the bandwidth of irradiating radiation and the Raman shift values desired to be distinguished).

A tunable filter is useful when Raman scattering measurements at multiple wavelengths at multiple locations simultaneously and when a Raman spectrum is to be obtained using the detector (e.g., for collecting 2-dimensional RS data from a sample). A variety of filter mechanisms are available that are suitable for these purposes. For example, an Evans split-element liquid crystal tunable filter (LCTF) such as that described in U.S. Pat. No. 6,002,476 is suitable. An LCTF can be electronically controlled to pass a very narrow wavelength band of light. The spectral resolving power of 8 $cm^{-1}$ (0.25 nanometer) is suitable to perform Raman spectroscopy, and the image fidelity is sufficient to take full advantage of the resolving power of a light microscope, yielding a resolution of better than 250 nanometers. Other suitable filters include Fabry Perot angle-rotated or cavity-tuned liquid crystal (LC) dielectric filters, other LC tunable filters (LCTF) such as Lyot Filters and variants of Lyot filters including Solc filters, acousto-optic tunable filters, and polarization-independent imaging interferometers such as Michelson, Sagnac, Twynam-Green, and Mach-Zehnder interferometers.

Pathogen particles to be analyzed as described herein can be placed on and secured to a surface to prevent movement during analysis. This is particularly important if Raman spectroscopy and light microscopy data are to be combined, because it is important to be able to correlate the microscopic characteristics of the pathogen particles, as directly or indirectly (e.g., using computer-processed or -stored image data) observed with the Raman scattering exhibited by the same particles. Particles can be secured or fixed on a surface using substantially any known technique, and any reagents known to exhibit strong Raman scattering at RS values characteristic of a pathogen of interest should be avoided or accounted for in scattering intensity determinations. Pathogens can be secured or fixed as individual particles on a substrate, as a substantially flat layer of particles on a substrate, or as a three-dimensional mass of particles. When a secured or fixed particle preparation includes particles at different elevations above the surface of the substrate, spatial analysis of the preparation is possible using known adaptations to light microscopy and Raman scattering methods. By way of example, Raman scattering can be correlated with height above the substrate by assessing Raman scattering using different planes of focus. Information obtained at the various planes can be reconstructed (e.g., using a computer for storage and display of the information) to provide a two- or three-dimensional representation of the sample.

Combining Raman Analysis and Other Optical Techniques

The methods described herein for assessing Raman scattering characteristics of pathogen particles that may occur in a water sample can be supplemented with other optical techniques for assessing the particles. By way of example, data from light microscopy of a sample can be combined with Raman scattering data, as shown in FIGS. 8 and 9. Alternatively, or in addition, data generated from fluorescence spectroscopy can be combined with Raman scattering data to further characterize the Raman scattering particles.

Raman scattered light can be assessed at individual points in a sample, or an optical image of the Raman scattered light can be generated using conventional optics. The Raman data or image can be visually displayed alone or in combination with (e.g., superimposed upon) a microscopic image of the sample. Conventional methods of highlighting selected Raman data (e.g., by color coding or modulating the intensity of Raman scattered light) can be used to differentiate Raman signals arising from various parts of the sample. By way of example, the intensity of Raman scattered light having a Raman shift of 2930 $cm^{-1}$ can be displayed in varying shades or intensity of green color, superimposed on a brightfield image of the sample. In this way, Raman scattering can be correlated with microscopic landmarks in the sample.

Combining Raman spectroscopy and visual light microscopy techniques enhances the usefulness of each by adding context to the information generated by the separate methods. Thus, morphological and structural information derivable from microscopic examination can be understood in the context of the biochemical makeup of the corresponding cellular materials and Raman scattering-based clues to the identity of particles detected in a water sample. Under appropriate circumstances, staining or labeling reagents can be used in combination with Raman scattering and light microscopy in order to yield further information about the particles.

Substantially any Raman spectrometer capable of defining, detecting, or capturing data from water samples (including residues from dried, filtered, or concentrated water samples) can be used to generate the Raman scattering data described herein. Likewise, substantially any light microscopy instrument can be used to generate visible light microscopy information. In circumstances in which positions of particles in the sample can be correlated (e.g., by analysis of particle positions and/or morphologies or by analysis of indicia on or shape of the substrate), it is not necessary that the Raman and microscope be integrated. In such circumstances, the data collected from each instrument can be aligned from separate observations. Preferably, however, a single instrument includes the Raman spectroscopy and light microscopy functionalities, is able to perform both analyses on a sample within a very short time period, and is able to correlate the spatial positions assessed using the two techniques. Information gathered using such an instrument can be stored in electronic memory circuits, processed by a computer, and/or displayed together to provide a depiction of the cell sample that is more informative that the separate depictions of the information obtained by the two techniques. A suitable example of equipment having these characteristics is the FALCON (RTM) RMI microscope available from ChemImage Corporation (Pittsburgh, Pa.). Suitable instruments are also described in U.S. Pat. No. 6,002,476 and in co-pending U.S. patent application Ser. No. 09/619,371.

An example of a probe suitable for in vivo analysis of cells in a bulk water sample is described in co-pending U.S.

patent application Ser. No. 10/184,580 (publication no. US 2003/0004419 A1, which is incorporated herein by reference). The tip of the probe can be inserted into a water sample and Raman scattering and visible microscopic image data can be collected therefrom, optionally at various discrete depths using focusing techniques and/or at various RS values. Substantially any fiber optic or other optical probe that can deliver irradiation to a sample and collect Raman light scattered therefrom can be adapted to an appropriate Raman spectrometer to perform the methods described herein. The probe preferably also includes an optical channel (e.g., a common optical fiber or a separate one) to facilitate microscopic imaging of the same sample for which Raman spectroscopy is performed.

Information generated from Raman spectroscopy and/or light microscopy as described herein can be stored in electronic memory circuits, such as those of a computer, for storage and processing. A wide variety of data analysis software packages are commercially available. Suitable types of software include chemometric analysis tools such as correlation analysis, principle component analysis, factor rotation such as multivariate curve resolution, and image analysis software. Such software can be used to process the Raman scattering and/or visible image data to extract pertinent information that might otherwise be missed by univariate assessment methods.

EXAMPLES

The invention is now described with reference to the following Examples. These Examples are provided for the purpose of illustration only, and the invention is not limited to these Examples, but rather encompasses all variations which are evident as a result of the teaching provided herein.

Figure 4:
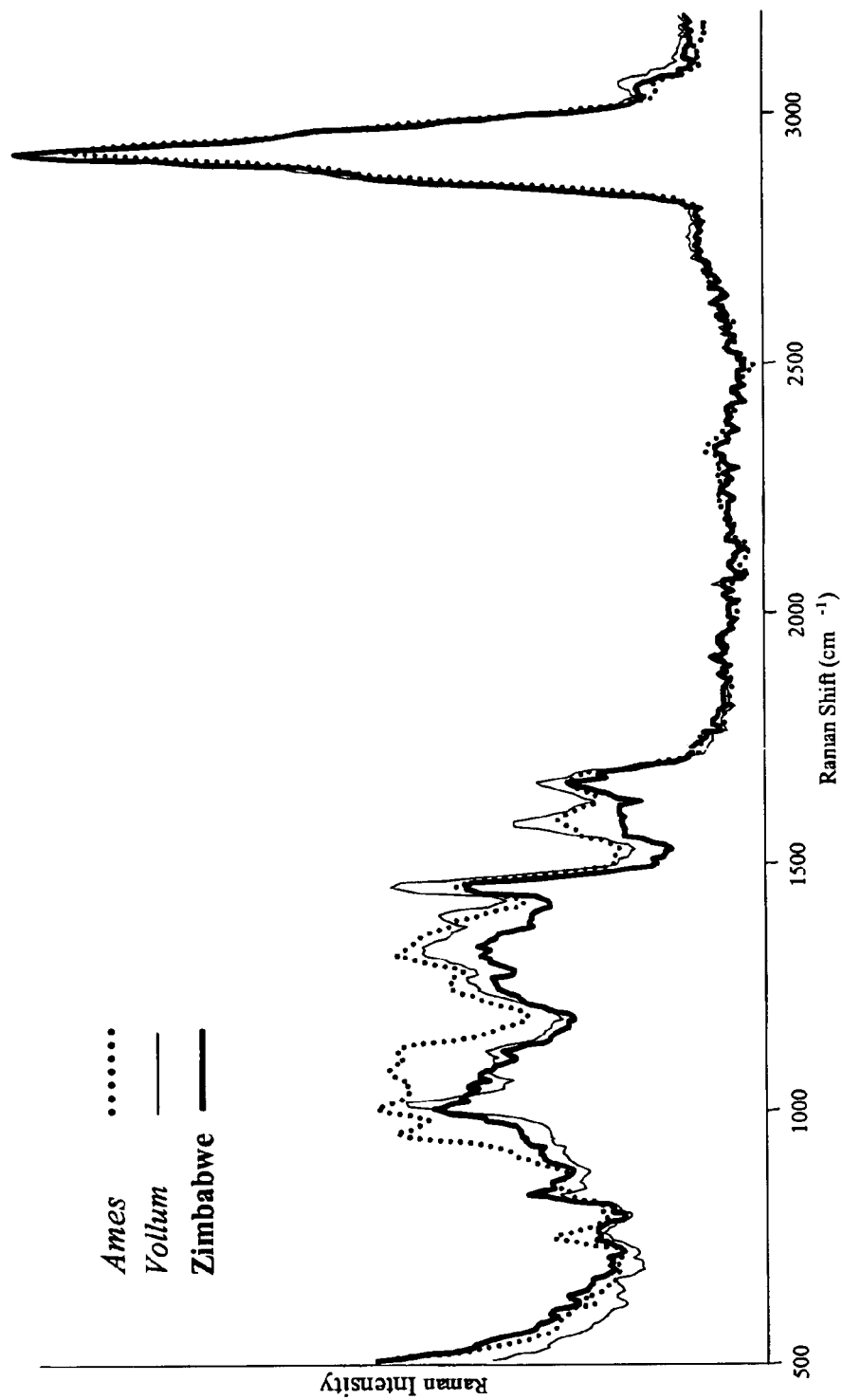

FIG. 4 shows how fluorescence spectroscopic imaging can be used to distinguish between bacteria spore types. The fluorescence spectra in the lower portion of the figure were obtained from the color-coded boxed regions in the concatenated fluorescence spectroscopic images above. It can be seen that *Bacillus subtilis* spores and *Bacillus pumilus* spores exhibit fluorescence peaks maxima at 540 nm and 630 nm, respectively.

Advanced image analysis and chemometric tools take these differences in fluorescence spectra and perform a spatial identification of species, producing the image in FIG. 4. The following is a representative algorithm for performing this analysis:

1) Divide the raw image by a background image (taken without the sample)
2) Do cosmic filtering on the resultant image (median filtering for pixels whose value differs significantly from the mean of a local neighborhood)

3) Use an alignment procedure to correct for slight movements of the sample during data collection 4) Apply a spatial average filter 5) Perform a spectral normalization (helps correct for varying illumination across the sample)

6) Perform a spectral running average over each set of three spectral points
7) Extract a set of frames corresponding to 550 to 620 nm. The spectra for both bacterial spores (*Bacillus subtilis* var *niger* and *Bacillus pumilus*) are essentially linear over this range. *Bacillus subtilis* var *niger* has a positive slope and *Bacillus pumilus* has a negative slope.
8) Create a single frame image in which each intensity value is the slope of the spectral sub-region (from the last image). The slope is determined via a least-squares fit.
9) Scale the resulting image between 0 and 4095. Keep track of the point from 0 to 4095 that corresponds to 0 in the prior image (the "Zero point").
10) Create a mask image from a series of steps:

10a) From the aligned image ($3^{rd}$ step), calculate a single frame "brightest" image in which the intensity of each pixel is the maximum intensity value for each spectrum.

10b) Scale this brightest image between 0 and 4095.

10c) Create a binarized image from the scaled image, in which every pixel whose intensity is greater than 900 is set to 1 in the new image and every pixel whose intensity is less than 900 is set to 0 in the new image. The value of 900 was chosen by an examination of the histogram associated with the scaled image. A future improvement to the algorithm would be to automatically select the threshold by numerically analyzing the histogram for a given image.

11) Multiply the scaled image from step 9 by the mask image from step 10. This restricts the visual display to only areas that correspond to spores. The result is a gray scale image in which intensity values below the zero point defined in step 9 correspond to *bacillus pumilus* and the intensity values above the zero point correspond to *bacillus subtilis* var *niger.*

The final RGB image is then created by setting all the "negative" values to red and all the "positive" values to green. A similar algorithm can be used to correlate Raman scattering data with a microscopic image.

An Iowa bovine isolate of *C. parvum* oocysts was obtained from experimentally infected calves (Waterborne, Inc., New Orleans, La.). The oocysts were obtained in suspension in distilled water, washed with distilled water, and deposited onto an aluminum-coated glass slide of the type typically used for Raman spectroscopy. A microscopic image and dispersive Raman spectrum of the oocysts are shown in FIGS. 6, 8, and 9. The same oocysts, which had been washed with and suspended in a river water sample are shown in the image and spectra shown in FIG. 7.

The data in FIG. 10 demonstrate that Raman spectral analysis can be used to differentiate between viable and non-viable *C. parvum* oocysts. These oocysts were suspended in a solution comprising 5% (v/v) formalin and 0.01% (v/v) TWEEN 20 (RTM) detergent to render the oocysts non-viable.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of assessing occurrence of a *Cryptosporidium* oocyst in an aqueous sample, the method comprising irradiating the sample and assessing radiation scattered from the sample for radiation that exhibits a Raman scattering characteristic of *Cryptosporidium* oocysts, wherein detection of scattered radiation that exhibits a Raman shift (RS) characteristic of *Cryptosporidium* oocysts is an indication that a *Cryptosporidium* oocyst occurs in the sample.

2. The method of claim 1, wherein detection of scattered radiation comprises detection of scattered light that exhibits a Raman shift (RS) value selected from the group consisting of RS values in the range from 500 to 3250 $cm^{-1}$.

3. The method of claim 2, comprising assessing scattered radiation at a plurality of RS values in the range.

4. The method of claim 1, wherein detection of scattered radiation comprises detection of scattered light that exhibits an RS value selected from the group consisting of RS values in the range from about 1000 to 1700 cm$^{-1}$ and RS values in the range from 2700 to 3200 cm$^1$.

5. The method of claim 1, wherein the Raman scattering characteristic is an RS value selected from the group consisting of RS values of about 1000, 1080, 1310, 1330, 1450, 1660, 2720, and 2930 cm$^{-1}$.

6. The method of claim 5, wherein the Raman scattering characteristic is at least two of the RS values.

7. The method of claim 5, wherein the Raman scattering characteristic is a ratio of two of the RS values.

8. The method of claim 1, wherein the Raman scattering characteristic is a Raman spectrum over at least a portion of RS values in the range from 500 to 3250 cm$^{-1}$.

9. The method of claim 1, wherein the Raman scattering characteristic is a Raman scattering characteristic of viable *Cryptosporidium* oocysts.

10. The method of claim 9, wherein the Raman scattering characteristic is a Raman scattering characteristic of non-viable *Cryptosporidium* oocysts.

11. The method of claim 9, wherein the Raman scattering characteristic is an RS value selected from the group consisting of 970, 1000, 1050, and 1610 cm$^{-1}$.

12. The method of claim 1, comprising comparing i) Raman scattered light emitted from the sample with ii) a reference value corresponding to Raman scattered light emitted from a sample of the same type that does not comprise *Cryptosporidium* oocysts.

13. The method of claim 1, comprising comparing i) Raman scattered light emitted from a portion of the sample which exhibits a non-Raman optical property characteristic of *Cryptosporidium* oocysts with ii) Raman scattered light emitted from a portion of the sample which does not exhibit the property.

14. The method of claim 13, wherein the property is appearance in an microscopic image of a roughly spherical body having a diameter in the approximate range from 2 to 6 micrometers.

15. The method of claim 13, comprising comparing i) Raman scattered light emitted from a first portion of the sample which, in a microscopic image, comprises a roughly spherical body having a diameter in the approximate range from 2 to 6 micrometers and ii) Raman scattered light emitted from a first portion of the sample which, in a microscopic image, does not comprise such a body.

16. The method of claim 1, wherein the sample is irradiated with substantially monochromatic visible light.

17. The method of claim 1, wherein the sample is irradiated with polarized radiation.

18. The method of claim 1, wherein radiation scattered by the sample is assessed directly from the aqueous sample.

19. The method of claim 1, wherein the sample is dehumidified prior to assessing radiation scattered by the sample.

20. The method of claim 19, wherein the sample is substantially dried prior to assessing radiation scattered by the sample.

21. The method of claim 20, wherein the sample is substantially dried on a Raman enhancing surface.

22. The method of claim 21, wherein the surface comprises a colloidal metal.

23. The method of claim 1, wherein the sample is contacted with a porous substrate assessing radiation scattered by the sample.

24. The method of claim 23, wherein the substrate substantially excludes particles having a characteristic dimension of at least about 2 micrometers.

25. The method of claim 23, wherein the substrate is an ultrafiltration membrane having a pore size not greater than about 1 micrometer.

26. The method of claim 1, wherein the *Cryptosporidium* oocysts are selected from the group consisting of *Cryptosporidium parvum* oocysts, *Cryptosporidium muris* oocysts, *Cryptosporidium meleagridis* oocysts, *Cryptosporidium wrairi* oocysts, *Cryptosporidium felis* oocysts, *Cryptosporidium serpentis* oocysts, *Cryptosporidium nasorum* oocysts, *Cryptosporidium baileyi* oocysts, *Cryptosporidium sarophilum* oocysts, *Cryptosporidium canis* oocysts, and *Cryptosporidium andersoni* oocysts.

27. A method of assessing occurrence of a viable *Cryptosporidium* oocyst in an aqueous sample, the method comprising irradiating the sample and assessing radiation scattered from the sample for radiation that exhibits a Raman scattering characteristic of viable *Cryptosporidium* oocysts, wherein detection of scattered radiation that exhibits a Raman shift characteristic of *Cryptosporidium* oocysts is an indication that a viable *Cryptosporidium* oocyst occurs in the sample.

28. A method of ablating viable *Cryptosporidium* oocysts in a sample, the method comprising identifying a viable *Cryptosporidium* oocyst in a portion of the sample by irradiating the sample, assessing radiation scattered from the sample for radiation that exhibits a Raman scattering characteristic of viable *Cryptosporidium* oocysts, and thereafter delivering an ablating agent to the portion.

29. The method of claim 28, wherein the ablating agent is radiation.

30. A method of eliminating viable *Cryptosporidium* oocysts from a sample, the method comprising identifying portions of the sample which comprise a viable *Cryptosporidium* oocyst by irradiating the sample, assessing radiation scattered from the sample for radiation that exhibits a Raman scattering characteristic of viable *Cryptosporidium* oocysts, and thereafter delivering an ablating agent to each portion which comprises a viable *Cryptosporidium* oocyst.

31. A method of assessing whether a *Cryptosporidium* oocyst in an aqueous sample is viable, the method comprising irradiating a portion of the sample that includes the oocyst and assessing radiation scattered from the portion for radiation that exhibits a Raman scattering characteristic of viable *Cryptosporidium* oocysts, wherein detection of radiation scattered from the portion that exhibits a Raman shift characteristic of viable *Cryptosporidium* oocysts is an indication that the oocyst is viable.

32. A method of assessing the source of cryptosporidial contamination of a water source, the method comprising identifying oocysts of a *Cryptosporidium* species by irradiating a sample of water from the source and assessing radiation scattered from the sample for radiation that exhibits a Raman scattering characteristic of a particular species of *Cryptosporidium* oocysts, whereby the species of *Cryptosporidium* oocysts can be correlated with a common host of that species to identify a likely source of the oocysts.

* * * * *